United States Patent [19]

Umetsu et al.

[11] Patent Number: 5,133,936
[45] Date of Patent: Jul. 28, 1992

[54] CONSTANT-TEMPERATURE AIR TYPE AUTOMATIC ANALYSIS APPARATUS

[75] Inventors: Hiroshi Umetsu, Katsuta; Hiroshi Hashimoto, Naka; Hajime Betsui, Katsuta, all of Japan

[73] Assignee: Hitachi, Ltd., Tokyo, Japan

[21] Appl. No.: 635,429

[22] Filed: Jan. 4, 1991

Related U.S. Application Data

[63] Continuation of Ser. No. 403,370, Sep. 6, 1989, abandoned.

[30] Foreign Application Priority Data

Sep. 7, 1988 [JP] Japan ................. 63-222378

[51] Int. Cl.⁵ ............... G01N 21/00; G01N 35/00; C12M 1/38
[52] U.S. Cl. .................... 422/64; 422/68.1; 436/50; 436/55; 435/290
[58] Field of Search ............... 422/63–68.1, 422/72, 73, 101, 102, 104; 436/46, 50, 55; 435/289, 290

[56] References Cited

U.S. PATENT DOCUMENTS

| 4,045,179 | 8/1977 | Bunce ................. 422/58 |
| 4,200,607 | 4/1980 | Suzuki ................ 422/64 |
| 4,676,952 | 6/1987 | Edelmann et al. ........ 422/64 |
| 4,696,187 | 9/1987 | Kopp et al. ............ 422/70 |
| 4,708,886 | 11/1987 | Nelson ................ 422/72 |
| 4,774,055 | 9/1988 | Wakatake et al. ........ 422/73 |
| 4,795,613 | 1/1989 | Azuma et al. ........... 436/46 |
| 4,855,109 | 8/1989 | Muraishi et al. ........ 422/65 |
| 4,858,155 | 8/1989 | Okawa et al. .......... 422/63 |
| 4,865,986 | 9/1989 | Coy et al. ............ 422/63 |

FOREIGN PATENT DOCUMENTS

56-168553 12/1981 Japan.
126508 5/1989 Japan.

Primary Examiner—James C. Housel
Assistant Examiner—William Chan
Attorney, Agent, or Firm—Fay, Sharpe, Beall, Fagan, Minnich & McKee

[57] ABSTRACT

A constant-temperature air type automatic analysis apparatus includes: a reaction table for rotating a row of reaction containers; a batch injecting device for supplying a sample and a reagent into the reaction containers; a photometric device for measuring a reaction within the reaction containers; a constant-temperature air device for keeping the reaction containers warm, the constant-temperature air device having an annular constant-temperature air chamber which is formed in such a manner as to surround the row of reaction containers; a heat block disposed within the annular constant-temperature air chamber; and a preliminary temperature raising device for heating the reaction containers. The preliminary temperature raising device has an air circulation passage, a blowing device for blowing a constant-temperature air against the reaction containers in a region between a injection position of the batch injecting device and a measuring position of the photometric device. Alternatively, the preliminary temperature raising device has a ventilating device for temporarily ventilating the air circulation passage.

12 Claims, 4 Drawing Sheets

CONSTANT-TEMPERATURE AIR TYPE AUTOMATIC ANALYSIS APPARATUS

This application is a continuation of application Ser. No. 403,370, filed Sept. 6, 1989 now abandoned.

BACKGROUND OF THE INVENTION

The present invention relates to an automatic analysis apparatus, and more particularly, to an automatic analysis apparatus provided with the function of keeping the temperature of a row of reaction containers constant.

In a conventional automatic analysis apparatus, an organic sample such as blood is generally measured by means of a photometer after preparing a reaction solution in which the sample and a reagent interact with each other. Measurements of a sample on a large number of analysis items are, for example, performed by using a discrete-type automatic analysis apparatus in which the reaction solution is generated in the reaction container, which is also used as a photometric cell, for each analysis item.

Reaction of the organic samples needs to be performed at a temperature which is kept constant in the vicinity of 37° C. Accordingly, it has been proposed to employ a constant-temperature water bath as a constant-temperature device and to immerse a row of reaction containers in the constant-temperature water. Such an automatic analysis apparatus is disclosed in the specification of Japanese Patent Laid-Open No. 56-168553.

In the above-described type of conventional automatic analysis apparatus in which the constant-temperature water bath is employed as the constant-temperature device, constant-temperature water is circulated between a constant-temperature water supply portion for supplying constant-temperature water and a bath. This requires much space, and therefore increases the overall size of the analysis apparatus.

Furthermore, it is better that a desk-top automatic analysis apparatus employ a constant-temperature air device in place of the constant-temperature water device. However, since the heat capacity of air is smaller than that of water, it takes a long time (e.g., 30 minutes) for a constant-temperature air bath having a heat block therein to raise the temperature of the solution injected into the reaction containers to 37° C., and this results in a prolongation of the overall analysis time.

SUMMARY OF THE INVENTION

An object of the present invention is to provide an automatic analysis apparatus which enables the temperature of the solution injected into a reaction container to be raised to a predetermined degree in a relatively short period of time by the use of a constant-temperature air bath and which enables it to be kept constant thereafter.

To this end, the present invention provides an automatic analysis apparatus which comprises a reaction table for rotating a row of reaction containers, a batch injection means for supplying a sample and a reagent to the reaction containers, a photometric means for measuring the reaction within the reaction containers, a constant-temperature air means for keeping the reaction containers warm, the constant-temperature air means having an annular constant-temperature air chamber which is formed in such a manner as to surround the row of reaction containers, a heat block disposed within the annular constant-temperature air chamber, and a preliminary temperature raising means for heating the reaction containers. The preliminary temperature raising means has an air circulation passage, and a blowing means for blowing constant-temperature air against the reaction containers in a region between a injection position of the injecting means and a measuring position of the photometric means. Furthermore, the preliminary temperature raising means has a ventilating means for temporarily ventilating the air circulation passage.

In the present invention, the temperature of the solution within the reaction container can be raised to a fixed value in a short period of time by means of a constant-temperature air bath, and this results in a reduction in the time required for analysis and an improvement in the sample measurement accuracy.

DESCRIPTION OF THE PREFERRED EMBODIMENTS

An embodiment of the present invention will be described below with reference to the accompanying drawings.

Figure 2:
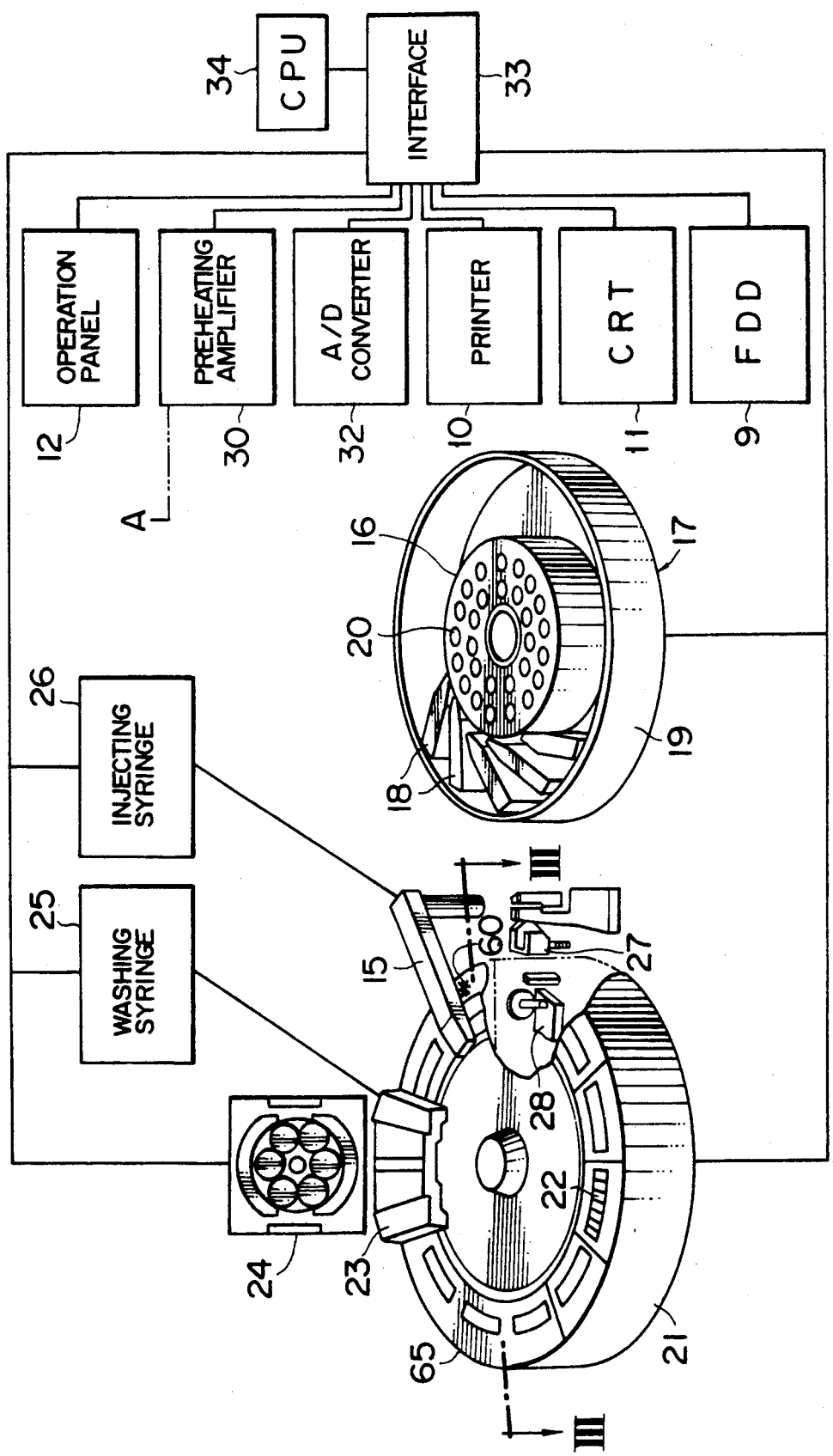
FIG. 2 is a schematic view of an automatic analysis apparatus with the preliminary temperature raising means of FIG. 1.

Referring first to FIG. 2, an automatic analysis apparatus according to the present invention includes a sample/reagent disk mechanism, a reaction disk mechanism, a batch injection mechanism, and a washing mechanism. The sample/reagent disk mechanism includes a sample table and a reagent table.

Reagent containers 18 are held on the reagent table 17 within a reagent insulating case 19. The sample table 16 is mounted on the reagent table 17 separately from the reagent insulating case 19. Sample containers are aligned in two rows on the sample table 16 in the circumferential direction thereof. Both the reagent table 17 and the sample table 16 are driven by a driving motor (not shown) through the same driving shaft. The reaction disk mechanism includes a reaction table 65, a constant-temperature reaction tank 21, and reaction containers 22. It also includes a washing mechanism 23 for drawing the reaction solutions within the reaction containers 22 and ejecting washing fluid to wash the reaction containers. A peristaltic pump 24 is used to draw the reaction solutions, and ejection of the washing fluid is performed by means of a washing syringe 25.

Between the sample/reagent disk mechanism and the reaction disk mechanism is disposed the batch injecting mechanism 15 for drawing the reagents in the reagent containers 18 and the samples in the sample containers 20 and for conveying them to and ejecting them at an ejection position 60 on the reaction container row. There drawing in and ejecting operations are performed by an injecting syringe 26, which is connected to a probe mounted on the forward end of an arm of the batch injection mechanism 15 through a tube. A probe washing tank 27 is disposed on the rotational locus of the probe on the side of the injection mechanism 15 which is closer to the front of the apparatus, and a fluorometer 28 for measuring the fluorescent radiation emitted by the reaction solutions is disposed within the constant-temperature reaction tank 21 on the rotational locus of the reaction containers 22.

Figure 1:
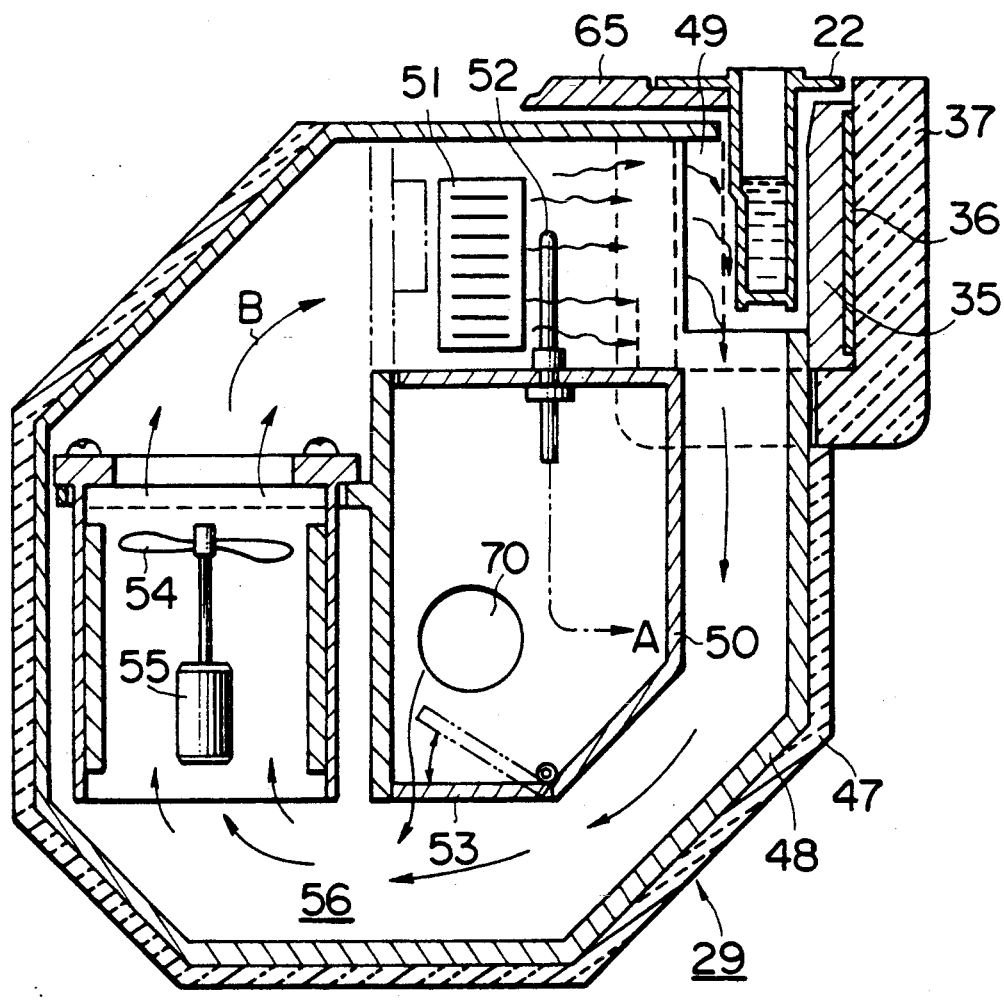
FIG. 1 is a cross-sectional view of a preliminary temperature raising means of an automatic analysis apparatus, showing an embodiment of the present invention.

A preliminary temperature raising means 29 shown in FIG. 1 is disposed between the position 60 at which reagents are ejected by the batch injecting mechanism 15 and the fluorometer 28 so as to raise the low temperature of the reagents to 37° C. by the time the reagents rotate clockwise from the position 60 and reach the fluorometer 28. The preliminary temperature raising means has a forced circulation preheating function. Temperature control of the preliminary temperature raising means is performed by a preheating amplifier 30. A printer 10, a CRT 11, an operation panel 12, a floppy disk drive (FDD) 9, an analog/digital converter 32 for processing the signal output from the fluorometer 28, and the preheating amplifier 30 are connected to be controlled by a CPU 34 through an interface 33.

Next, the operation of the automatic analysis apparatus shown in FIG. 2 will be described below. Organic solutions such as blood serums or blood plasmas containing antigen or urea are used as samples. Normally used reagents are employed. In particular, reagent solutions containing a solid phase with an antibody coated thereon are employed for analyzing the immune reaction or like of a virus. First, a large number of sample containers 20 are held on the sample table 16, and the reagent containers 18 are cooled at a predetermined temperature in the reagent insulating case 19. A predetermined amount of sample is drawn from the sample container 20 on the sample table 16 by means of the probe of the batch injection mechanism 15 and is conveyed to and ejected into the reaction containers 22 located at the designated position 60 on the reaction table 65. After the ejection, the probe of the injection mechanism 15 is sufficiently washed by the probe washing tank 27 so as to prevent contamination of the sample solutions. Thereafter, the reaction table 65 is vibrated for a few seconds by a vibration driving means so as to stir the reaction solution, and the row of reaction containers is then rotated.

Figure 4:
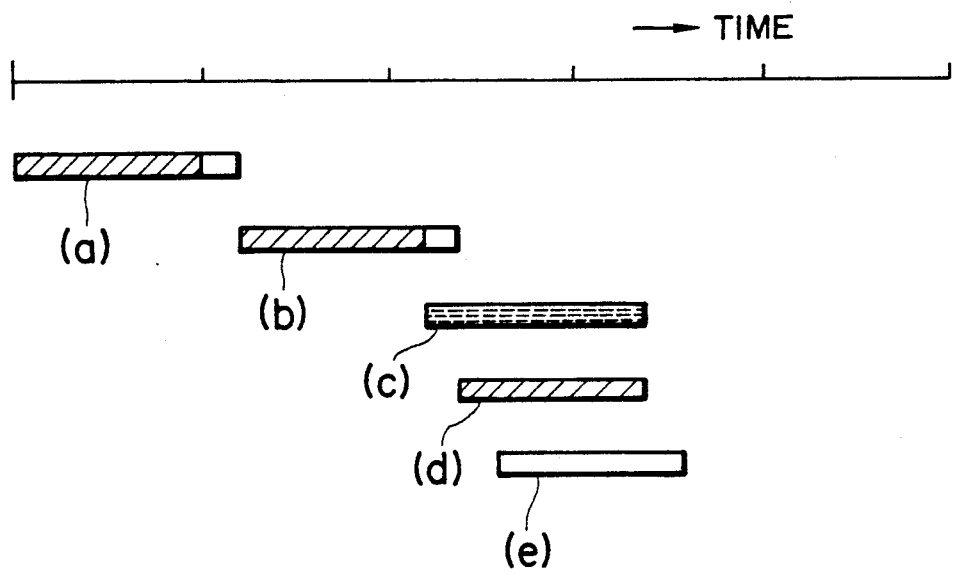
FIG. 4 shows a time chart of the analysis process of the automatic analysis apparatus according to the present invention.

A sequence of the above-described operations is repeated until a required number of samples are conveyed into the reaction containers 22. This process is indicated by (a) in FIG. 4. Next, the reagent is drawn from the reagent container 18 by the injection mechanism 15 and is conveyed to and ejected into the reaction container 22 located at the ejection position 60. In one injection cycle, reagents in a reagent system are conveyed and batch injected in sequence, starting with the first reagent. The process is indicated by (b) in FIG. 4. Thus, the samples and reagents are batch-injected into the reaction containers 22 while the reaction table 65 is being rotated.

The reaction containers 22 are kept at a predetermined temperature, e.g., 37° C., by means of the constant-temperature reaction tank. Reaction of the samples with the reagents can be performed in a stable state in the constant-temperature tank. This enables highly sensitive measurement of the reaction.

Figure 3:
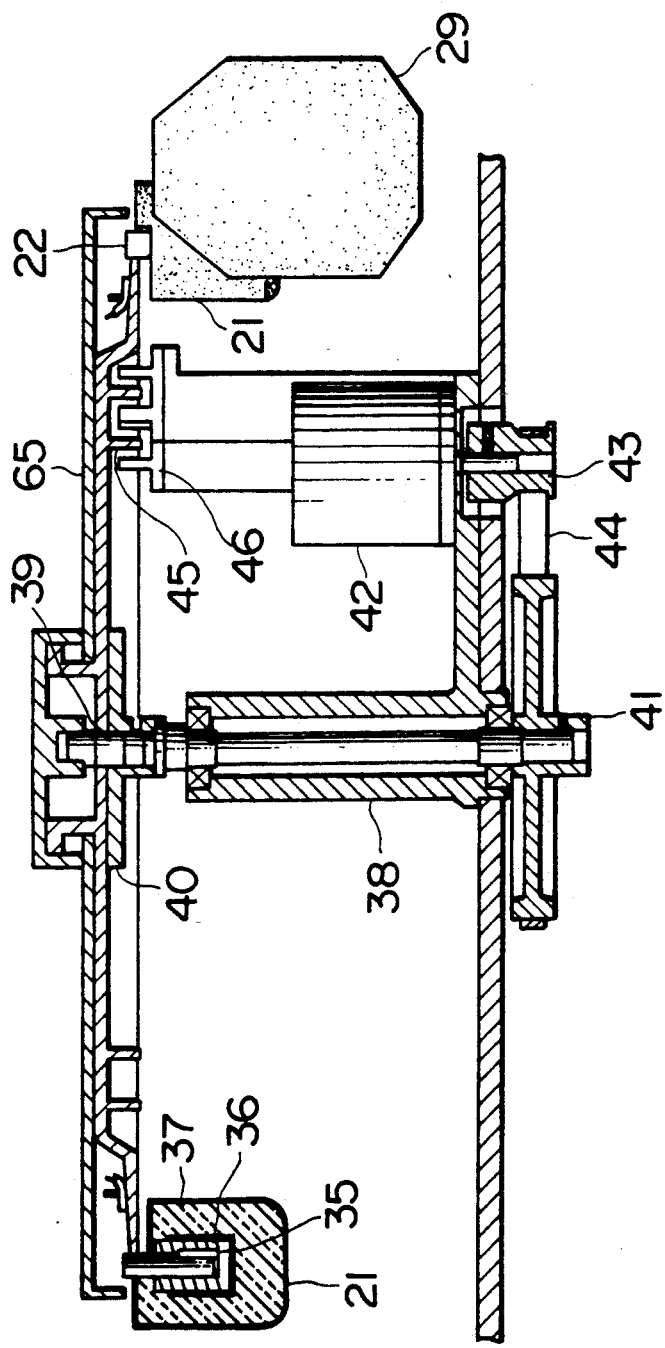
FIG. 3 is a section taken along the line 3—3 of FIG. 2.

FIG. 3 is a cross-sectional view of the constant-temperature air tank with the preliminary temperature raising means 29 incorporated therein. The constant-temperature air tank 21 has an annular chamber which is formed in such a manner as to surround the reaction container row. The annular constant-temperature air tank is provided near the periphery of and below the reaction table 65. The reaction containers 22 hang into the interior of the constant-temperature air tank 21 in a row. The annular chamber has a form which allows the row of reaction containers to be rotated therealong. The temperature of the entire constant-temperature air tank is kept at 37° C. by means of a metal heat block 35 having a U-shaped cross-section so that it can enclose the reaction containers except for the upper portions thereof. A sheet heater 36 is disposed on the outer periphery of the heat block 35 so as to supply heat.

The temperature of the reaction containers 22 held by the reaction table 65 is kept at 37° C. while the containers are accommodating reaction solutions. The outer periphery of the sheet heater 36 attached on the outer peripheral surface of the heat block 35 is covered by a heat insulating material 37, which is in turn covered by a cover. The reaction table 65 is fixed to a washer 40 mounted on a shaft 39 supported by a driving base 38. A pulley 41 mounted on the other end of the shaft 39 and a pulley 43 mounted on a pulse motor 42 are connected by a timing belt 44 so as to transmit the rotational force of the pulse motor 42 to the reaction table 65. The angle of rotation of the reaction table 65 is detected by a detection plate 45 formed integrally with the reaction table 65 and a photo-interrupter 46.

FIG. 1 is a cross-sectional view of the preliminary temperature raising means 29 having the forced preheating function. The preliminary temperature raising means 29 has an opening in the upper portion thereof. This opening 49 forms part of the accommodating portion or annular chamber 21 that surrounds the row of reaction containers 22. Thus, after the reaction container has received solution at the a solution receiving position 60, it is fed into the opening 49, as the reaction table is rotated, and is forcibly warmed. The temperature raising means 29 has a casing 48 which is opened at the opening 49. The casing 48 is in turn covered by a heat insulating material 47.

In the interior of the casing 48 is disposed a small casing 50. The space between the inner wall of the casing 48 and the outer wall of the small casing 50 forms a substantially circular annular air circulation passage 56. A ventilating hole 70 is opened to the interior of the small casing 50. Air which is introduced is used to control the temperature of the constant-temperature air tank. Air flows into the circulation passage 56 of the preliminary temperature raising means 29 when a lid member 53 mounted on the small casing 50 is opened through a predetermined angle by a driving mechanism (not shown). At the lower limit of the temperature control range, the lid member 53 is closed. Within the circulation passage are disposed a self-regulating type heater 51 such as a ceramic heater, a thermistor 52 for detecting the temperature, and a warmed air circulating fan 54 driven by a motor 55. This keeps the temperature of the air circulated in the circulation passage at 37° C. and keeps the circulated air blown against the reaction containers 22.

Reagent solutions containing an solid phase with the antibody coated thereon are set on the reagent table, and the sample solutions containing an antigen such as a virus are ejected into the reaction containers 22. Subsequently, the reagent solutions are added, and the reagent solutions and the sample solutions are vibrated and thereby stirred by means of the driving means, which includes the pulse motor 42, the pulley 43, the timing belt 44, the pulley 41 and the driving shaft 39, by controlling the driving signal applied to the pulse motor 42. The antigen and the solid phase are brought into contact each other, and the variable portion of the antibody reacts with the antigen. After a predetermined period of time has elapsed, the solid phase is washed away by the washing mechanism 23 (see FIG. 2), i.e., the non-reacted solution which is a source of noise in a highly sensitive measurement is discharged by the nozzle of the washing mechanism 23. Thereafter, the washing water is ejected from another nozzle by the operation of the washing syringe 25 for rewashing. This state is indicated by the process (c) in FIG. 4.

After the solid phase has been washed away, a substrate solution which is an enzyme reaction solution is added. At that time, the temperature of the mixture solution (reaction solution) within the reaction container is lowered below 37° C. After the addition of the substrate solution, the air which is kept at 37° C. by the preliminary temperature raising means 29 is blown against the reaction container 22 to raise its temperature and keep it at 37° C. This state is indicated by the process (d) in FIG. 4. When five minutes have passed after the addition of the substrate solution, the reaction state is measured by the fluorometer 28 so as to analyze the concentration of the components in the sample. This state is indicated by the process (e) in FIG. 4. In the time chart shown in FIG. 4, the reagent injection process (b) is programmed so that the number of processes can be increased or decreased according to the number of reagents required for reaction.

The automatic analysis apparatus according to the present invention may also be used as a diagnosis device for acquired immune deficiency syndrome (AIDS) because of its highly sensitive immune measurement. It is capable of detecting an antigen contained in a sample at a concentration of $10^{-6}$ to $10^{-13}$ mol/l. The analysis apparatus according to the present invention is about $10^6$ times more sensitive than the conventional biochemical analysis apparatus which is capable of detecting a antigen contained at a concentration of $10^{-6}$ mol/l. It is therefore essential to raise the temperature of the reaction solution to a predetermined degree as quickly as possible.

The flow of air in the forced circulation preheating function will be described in detail below with reference to FIGS. 1 and 3. The air is blown by the fan 54 in the direction indicated by the arrow B and toward the heater 51. The temperature of the air which has passed through the heater 51 is detected by the thermistor 52. The detection signal of the thermistor 52 is processed by a control circuit and is fed back as a heater voltage which keeps the temperature of the heater at 37° C. The thermistor 52 shown in FIG. 1 is connected to the preheating amplifier 30 shown in FIG. 2. The air which has passed through the heater 51 is blown against the reaction container 22 so as to raise the temperature of the interior of the reaction container to 37° C. in a short period of time. Thereafter, the air is further circulated by the fan 54. When the temperature of the air is raised excessively, the lid 53 is raised in response to the detection signal of the thermistor 52 so as to introduce the air.

Figure 5:
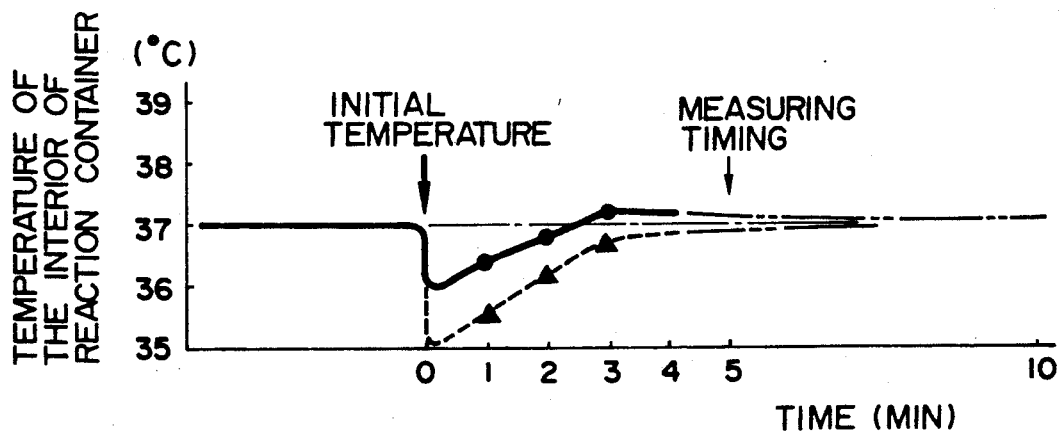
FIG. 5 shows how the temperature of the solution within the reaction container changes in the analysis apparatus according to the present invention.

FIG. 5 is a graph, showing how the temperature of the solution within the reaction container rises when the reaction container is conveyed to the preliminary temperature raising means after it has received a buffer solution (35° C.) and a substrate solution (about 20° C.) at the solution receiving position 60 on the reaction table 65. The temperature of the solutions accommodated in the reaction containers rises to 37° C. at which measurement by the fluorometer is possible, in five minutes. The temperature changes within the range surrounded by the solid line and the broken line when the ambient temperature is between 15° C. and 32° C.

In the above-described embodiment, the temperature of the solutions can be raised up to 37° C. in a short period of time by the use of the constant temperature air tank, with the shortcomings of the use of the conventional water bath eliminated. More, specifically, the present embodiment eliminates contamination by the bacteria generated in the water channel which is experienced by the conventional constant-temperature water tank, as well as the troublesome maintenance thereof. It also eliminates the possibility of the water spilling during the exchange of the reaction containers, and thus provides a simple, highly reliably apparatus.

What is claimed is:

1. A constant-temperature air type automatic analysis apparatus, comprising:
   a reaction table for containing a row of reaction containers;
   a batch injecting means for supplying a sample and a reagent into said reaction containers at a first position with respect to said reaction table;
   a photometric means for measuring a reaction within said reaction containers at a second position with respect to said reaction table;
   said reaction table having means for rotating said reaction containers from said first position to said second position;
   means for changing the temperature of said reaction containers to a predetermined temperature, wherein said temperature changing means has an air circulation passage and a blowing means for blowing air against the reaction containers to change the temperature of the reaction containers, said temperature changing means being located at a temperature changing station in said reaction table between said first and second positions; and
   a temperature holding means for holding said reaction containers at a constant temperature whenever they are displaced from the temperature-changing station, and for returning the reaction containers to said constant temperature whenever they deviate from said constant temperature, said temperature holding means comprising a temperature-regulated heat block contained within an annular chamber which is formed so as to surround said row of reaction containers.

2. An automatic analysis apparatus according to claim 1, wherein said temperature changing means is mounted on the under surface of said reaction table.

3. An automatic analysis apparatus according to claim 1, wherein said air circulation passage of said temperature changing means is substantially circular and annular.

4. An automatic analysis apparatus according to claim 1, wherein said air circulation passage incorporates an air blowing fan, a heater and a temperature detector.

5. An automatic analysis apparatus according to claim 1, wherein said air circulation passage is formed so as to blow against said reaction containers in a direction perpendicular to the advanced direction of said reaction containers.

6. A constant-temperature air type automatic analysis apparatus as claimed in claim 1, wherein said blows means locally blows air against a portion of said row of reaction containers for rapidly raising the temperature thereof by circulating a larger amount of air flow in the portion of the row of reaction containers heated by the preheating means than in the remainder of the row of reaction containers, said air flow being in a direction substantially perpendicular to the direction of transfer of the reaction containers from said first position to said second position, and wherein said heat block is constructed to maintain noncontactingly the reaction containers at a constant temperature.

7. A constant-temperature air type automatic analysis apparatus, comprising:
   a reaction table for containing a row of reaction containers;
   a batch injecting means for supplying a sample and a reagent into said reaction containers at a first position with respect to said reaction table;
   a photometric means for measuring a reaction within said reaction containers at a second position with respect to said reaction table;
   said reaction table having means for rotating the reaction containers from said first position to said second position;
   means for changing the temperature of said reaction containers to a predetermined temperature; wherein said temperature changing means has an air circulation passage and a blowing means for blowing air against the reaction container to change the temperature of the reaction containers, said temperature-changing means being located at a temperature changing station in a region between said first and second positions, said temperature changing means containing a venting means for temporarily venting said air circulation passage; and
   a temperature holding means for holding said reaction containers at a constant temperature whenever they are displaced from the temperature-changing station, and for returning the reaction containers to said constant temperature whenever they deviate from said constant temperature, said temperature holding means comprising a temperatureregulated heat block contained within an annular chamber which is formed so as to surround said row of reaction containers.

8. An automatic analysis apparatus according to claim 7, wherein said temperature changing means is mounted on the under surface of said reaction table.

9. An automatic analysis apparatus according to claim 2, wherein said air circulation passage of said temperature changing means is substantially circular annular.

10. An automatic analysis apparatus according to claim 7, wherein said air circulation passage incorporates an air blowing fan, a heater and a temperature detector.

11. An automatic analysis apparatus according to claim 7, wherein said air circulation passage is formed so as to blow against said reaction containers in a direction perpendicular to the advanced direction of said reaction containers.

12. A constant-temperature air type automatic analysis apparatus as claimed in claim 7, wherein said blows means locally blows air against a portion of said row of reaction containers for rapidly raising the temperature thereof by circulating a larger amount of air flow in the portion of the row of reaction containers heated by the preheating means than in the remainder of the row of reaction containers, said air flow being in a direction substantially perpendicular to the direction of transfer of the reaction containers from said first position to said second position, and wherein said heat block is constructed so as to maintain noncontactingly the reaction containers at a constant temperature.

* * * * *